(12) United States Patent
Mely et al.

(10) Patent No.: US 7,880,021 B2
(45) Date of Patent: Feb. 1, 2011

(54) COMPOUNDS AND KITS FOR THE DETECTION AND THE QUANTIFICATION OF CELL APOPTOSIS

(75) Inventors: Yves Mely, La Wantzenau (FR); Andrey Klymchenko, Strasbourg (FR); Oleksandr Demchenko, Kiev (UA); Vasyl Shynkar, Paris (FR)

(73) Assignees: Centre National de la Recherche Scientifique (CNRS), Paris (FR); Universite Louis Pasteur (Strasbourg I), Strasbourg (FR)

( * ) Notice: Subject to any disclaimer, the term of this patent is extended or adjusted under 35 U.S.C. 154(b) by 9 days.

(21) Appl. No.: 11/992,387

(22) PCT Filed: Oct. 11, 2006

(86) PCT No.: PCT/IB2006/003911

§ 371 (c)(1), (2), (4) Date: Mar. 21, 2008

(87) PCT Pub. No.: WO2007/057782

PCT Pub. Date: May 24, 2007

(65) Prior Publication Data

US 2009/0269793 A1      Oct. 29, 2009

Related U.S. Application Data

(60) Provisional application No. 60/724,772, filed on Oct. 11, 2005.

(51) Int. Cl.
C07D 311/04 (2006.01)
C07D 409/04 (2006.01)
C07D 409/00 (2006.01)
C12Q 1/02 (2006.01)

(52) U.S. Cl. ................ 549/400; 546/196; 546/155; 549/60; 549/23; 435/29

(58) Field of Classification Search .............. None
See application file for complete search history.

(56) References Cited

FOREIGN PATENT DOCUMENTS

WO      WO 03/105814 A      12/2003

OTHER PUBLICATIONS

Schellenberger et al. Optical Imaging of Apoptosis as a Biomarker of Tumor Response to Chemotherapy; Neoplasia, vol. 5, No. 3 (2003) pp. 187-192.*

Shynkar et al. Fluorescent Biomembrane Probe for Ratiometric Detection of Apoptosis; Journal of the American Chemical Society, vol. 129 (2007) pp. 2187-2193.*

Klymchenko et al. Ultrasensitive Two-Color Fluorescence Probes for Dipole Potential in Phospholipid Membranes; vol. 100, No. 20 (2003) pp. 11219-11224.*

Klymchenko et al. Novel Two-Band Ratiometric Fluorescence Probes With Different Location and Orientation in Phospholipid Membranes; Chemistry and Biology, vol. 9 (2002) pp. 1199-1208.*

International Search Report issued May 23, 2007 in corresponding PCT/IB2006/003911.

V. Shynkar et al., "Two-color Fluorescent Probes for Imaging the Dipole Potential of Cell Plasma Membranes" *Biochimica et Biophysica Acta*, Biomembranes, Amsterdam, NL, 1712(2)128-136 (Jul. 1, 2005).

* cited by examiner

*Primary Examiner*—Rebecca E. Prouty
*Assistant Examiner*—Paul C. Martin
(74) *Attorney, Agent, or Firm*—Buchanan Ingersoll & Rooney PC

(57) ABSTRACT

3-hydroxyflavone derivatives are useful in the detection and the quantification of cell apoptosis. Such derivatives are also useful as fluorescent probes in studying lipid asymmetry of cell plasma membrane and in detecting apopoptic cells. The derivatives can be used to monitor the evolution of diseases involving cell apoptosis.

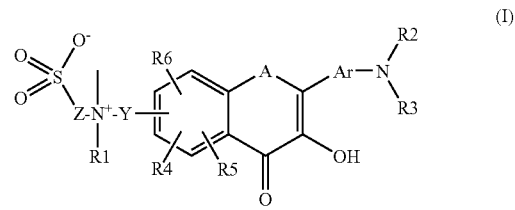

20 Claims, 8 Drawing Sheets

COMPOUNDS AND KITS FOR THE DETECTION AND THE QUANTIFICATION OF CELL APOPTOSIS

FIELD OF THE INVENTION

Figure 1:
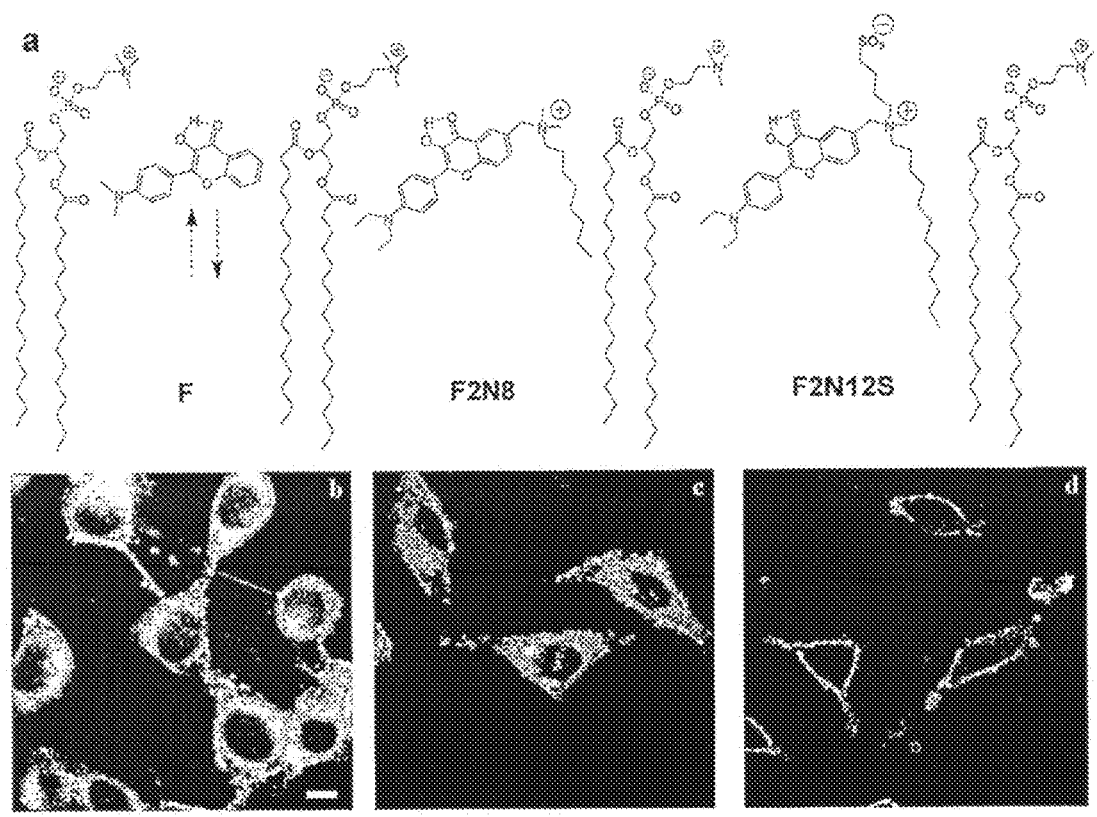

The present invention relates to the field of probes for the determination of cell apoptosis.

More specifically, the present invention relates to 3-hydroxyflavone (3-HF) derivatives and their use in biomembrane studies. It also relates to a method for the determination of cell apoptosis and a method to assay the degree of cell apoptosis involving the use of these compounds as a probe, a kit containing such compounds and their use as a probe in cytometry analysis for separating apoptotic, necrotic and living cells, respectively, and a method for following the evolution of a patient's disease involving the apoptosis of cells and the action of drugs capable of activating or modulating this process.

BACKGROUND OF THE INVENTION

Apoptosis is a programmed physiological mode of cell death that eliminates compromised or superfluous cells and that plays an important role in tissue homeostasis.

Apoptosis is involved in pathological conditions in which the delicate balance between cell proliferation and death is disturbed. Apoptosis can be induced by endocrine and other stimuli, negative selection in the immune system and a substantial proportion of T-cell killing. It also accounts for many cell deaths following exposure to cytotoxic compounds, hypoxia or viral infection. It is a major factor in the cell kinetics of tumours, both growing and regressing.

Many anti-cancer agents exert their effects through initiation of apoptosis, and even the process of carcinogenesis itself may depend upon a selective critical failure of apoptosis that permits the survival of cells after critical mutagenic DNA damage.

Apoptosis probably contributes to many chronic degenerative processes including Alzheimer's disease, Parkinson's disease and heart failure. Because of efficient multifactorial mechanism of cell death, apoptosis itself does not induce inflammatory response in vivo.

In contrast to apoptosis, necrosis is an accidental cell death due to chemical or physical injury of the cell membrane. Morphological criteria of necrosis include cell swelling (instead of shrinking), cell lysis, lysosomal leakage and loss of the membrane integrity. The cellular changes that are characteristic for apoptosis may also be found for necrosis.

Necrosis in pathology occurs when cells are exposed to extreme variance from physiological conditions (e.g.; hypothermia, hypoxia, strong UV and ionising radiation), which result in damage of plasma membrane. Necrosis is commonly accompanied by intense inflammatory response and tissue damage because of the leakage of the lysosomal enzymes into extra cellular fluid.

It is known that normal cells exhibit remarkable asymmetry of lipid distribution between inner and outer leaflets of cell membranes, which is lost during the early steps of apoptosis and necrosis. Most characteristic in this change is the exposure to cell surface of amine-containing phospholipids such as phosphatidylethanolamine (PE) and phosphatidylserine (PS). This exposure is functionally important as it provides the signal for recognition and elimination of apoptotic cells by macrophages. This change of cell membrane properties allows also to identify and characterize apoptotic cells.

One of the first approaches for the determination of cell apoptosis was based on the detection of the exposure of amino groups on the cell surface that can be detected by chemical reagents specific for amino groups. However, the low specificity of these reactions and their strong dependence on the environment limit their application in apoptosis research.

Therefore, more specific methods based on molecular recognition of surface-exposed PS and PE were developed.

The most popular of them is based on the property of annexin V to interact with PS exposed on the surface in a Ca2+-dependent manner. Different variants of this method were developed. For instance, in one of this variant, annexin V labelled with fluorescein was used for flow cytometry while annexin V labeled with red-near infrared dyes is used for tissue imaging. This protein was also labeled with colloid gold for electron microscopy, with radioactive tracer for autoradiography on the tissue level and with peroxidase for histochemical studies. In all these tests, a high (up to 2.5 mM) extracellular concentration of $Ca^{2+}$ ions has to be provided for complete binding of annexin V to PS. Since $Ca^{2+}$ ions activate the protein scramblase that randomises the phospholipids distribution, this enzyme can move PS to the cell surface in a calcium-dependent manner and lead to false positive results.

Furthermore, annexin V can associate with membrane surfaces containing by-products of lipid per oxidation that modify amines by producing negative charges.

Moreover, detergents in the medium can also change the annexin V lipid binding specificity.

In addition, routinely used cell harvesting techniques for adhering cells, such as trypsinization, can also produce false results in application of this method.

Finally, for complete annexin V binding, pre-incubation times of up to 1 h are in principle needed, making kinetic measurements problematic.

Alternative methods include application of monoclonal antibodies against negatively charged lipids. However, these antibodies found a limited application, probably because of their lability, high cost and complicated procedures for visualization of their binding. Moreover, it was shown that their binding inhibits Na/K-ATPase activity. Meantime, mimicking the behaviour of antibodies allowed to find peptides that can specifically recognize and bind PS and PE. Biotinilated peptides can be conjugated with fluorescently labeled streptavidin providing fluorescent labeling of apoptotic cells.

Tracing of lipid exchange between leaflets can also be made with the aid of fluorescently labeled lipids. However, intervening in the lipid distribution between leaflets is not well tolerated by the cells, and cell treatment with exogenic PS can itself induce apoptosis.

Probes for the exposure of PS on cell surface can be designed by synthetic organic chemistry. For instance, an organic molecule composed of a fluorophore and an artificial zinc-containing receptor for PS recognition was suggested for apoptosis detection. Providing a significant simplification of the detection procedure, this probe is still far from the ideal solution for detecting apoptotic cells, mainly because of the requirement for the presence of chelating ions in the medium.

The increase of the negative charge of apoptotic cells due to PS exposure can also be used for sensing. Cationic liposomes with incorporated fluorescent phospholipid analogs bind to apoptotic cells and provide their labeling. Based on the same principle of selective binding to negatively charged surface, some positively charged nanoparticles have been selected from chemically derived library.

The membrane-specific detection of apoptotic cells can be based on a quite different concept. The randomisation of lipid content should provide a decrease of lipid order and membrane rigidity. The small size of the lipid head of PE and the repulsion between negatively charged PS heads should increase hydration of the outer leaflet, and these changes can be detected by fluorescent dyes.

There are many observations that apoptotic cells exhibit increased binding of not only cationic amphiphilic drugs, such as chlorpromazine and verapamil, but also of the negatively charged lipophilic dye, merocyanine 540 (M540). This dye is known to bind most efficiently to structurally destabilized lipid bilayers and therefore can distinguish apoptotic cells. However, the approach based on M540 binding is rarely used because of its low specificity.

Therefore, another approach for the detection of cell apoptosis based on the change of order/hydration in the outer leaflet of cell membrane has been developed. This approach is focused on the unique properties of 3-hydroxyflavone (3HF) derivatives as environment-sensing dyes with two-color ratiometric response. These dyes were functionalised for binding to phospholipids membranes. This allowed observing a strong two-color response of fluorescence emission to variation of phospholipids composition. The most significant effect was due to variation of the surface charge observed in comparison between neutral and negatively charged phospholipids bilayers.

However, these 3-hydroxyflavone (3HF) derivatives are characterized by a rapid penetration inside the cells and present a low selectivity to cell plasma membranes.

The present inventors have thus underlined that the key problem for the selectivity of these 3-hydroxyflavone (3HF) compounds was to incorporate the dye selectively into the outer leaflet of the plasma membrane. The inventors' work demonstrated that this aim could be realized by coupling a long hydrocarbon chain and a zwitterionic group to the 3-HF moiety, in order to mimic the lipid structure and to place the fluorophore close to the membrane surface. The inventors have thus developed a new 3-HF compound that possesses a zwitterionic group and a long hydrocarbon chain which significantly diminishes the penetration rates of the probes through a bilayer. As a consequence, this compound is not redistributed into the cell interior and remains located in the cell plasma membrane.

Experiments by the present inventors have shown that, compared with the known non-invasive methods for the detection of apoptosis, the use of the new 3-HF compound as a probe for the detection of cell apoptosis presents the following advantages:

it is easier to handle and to prepare, it enables quantitative measurements that are independent on the local probe concentration, it requires shorter incubation times, and its response to apoptosis does not depend on the presence of $Ca^{2+}$ ions or on any other compound present in the cell environment.

The present invention will become better understood and other aspects, advantages, objectives of the present invention will become apparent from the following description taken in close conjunction with the accompanying figures. These are for illustration only, and thus are not to be considered as limiting the present invention.

DISCLOSURE OF THE INVENTION

The invention relates to a 3-hydroxyflavone (3-HF) compound having the general formula (1)

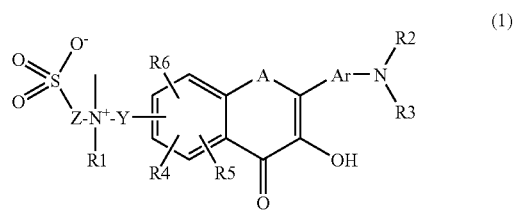

wherein:

R1 represents a linear alkyl group of 4 to 20 carbon atoms;

Y represents a linear alkylene group of 1 to 5 carbon atoms or a group of formula —R—O—R'—, —R—CO—R'— or —R—CO—NH—R'—, in which R represents a linear alkylene group of 1 to 3 carbon atoms, R' represents a linear alkylene group of 0-3 carbon atoms, Y being linked to the bicycle in position 6 or 7;

Z represents a linear alkylene chain of 3 or 4 carbon atoms;

A represents an oxygen atom, a sulphur atom, or a —N(H)— group, or an aminoalkyl group —N(R")— in which R" represents an alkyl group of 1 to 20 carbon atoms;

Ar represents an aromatic cycle or polycycle consisting of 6 to 14 carbon atoms, or an aromatic heterocycle, said heterocycle containing 4, 5 or 6 carbon atoms and at least one heteroatom selected in the group consisting of N, S, and O, or a condensed aromatic heterobicycle, said heterobicycle consisting of 6 to 9 carbon atoms and at least one heteroatom selected in the group consisting of N, S, and O;

R2 and R3, which are identical or different, each representing a hydrogen atom or an alkyl group of 1 to 8 carbon atoms, R2 and R3 optionally forming a 5- to 7-membered ring with the nitrogen atom;

R4, R5 and R6, identical or different, represent an hydrogen, a linear alkyl group or a linear oxyalkyl group of 1 to 4 carbon atoms.

Preferably, A represents an oxygen atom, a sulphur atom, or a —N(H)— group and R' is absent (represents a linear alkylene group of 0 carbon atoms).

Examples of aryl group Ar according to the invention include phenyl, naphtyl, furfuryl, benzofurfuryl, isobenzofurfuryl, pyrrolyl, indolyl, isoindolyl, indolizinyl, thienyl, benzothienyl, oxazolyl, pyrazolyl, thiazolyl, imidazolyl, triazolyl, pyridyl, quinolyl, isoquinolyl, phtalazinyl, naphtyridinyl, quinoxalinyl, quinazolinyl, cinnolinyl, pteridinyl, pyrazinyl, pyrimidinyl, purinyl, thieno[3,2-b]thiophene.

Among these aryl groups, mention may be made of phenyl, naphtyl, furfuryl, benzofurfuryl, isobenzofurfuryl, pyrrolyl, indolyl, isoindolyl, indolizinyl, thienyl, benzothienyl, pyrazinyl, pyrimidinyl.

Preferably, R4, R5 and R6 represent an hydrogen or a methyl, methoxy, ethyl or ethoxy group.

The compounds according to the invention are prepared as a racemic mixture. However, they can be further purified to separate each enantiomers.

Among the compounds of general formula (1) above which fall within the scope of the present invention, mention may be made in particular of the following compounds:

Compound of Formula (2)

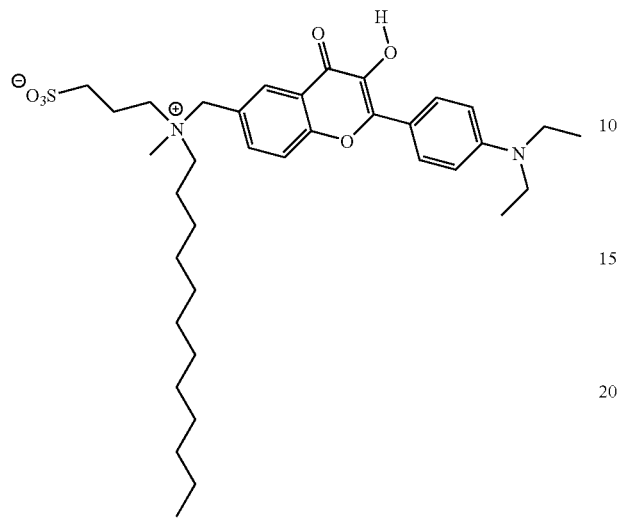

(2)

Compound of Formula (3)

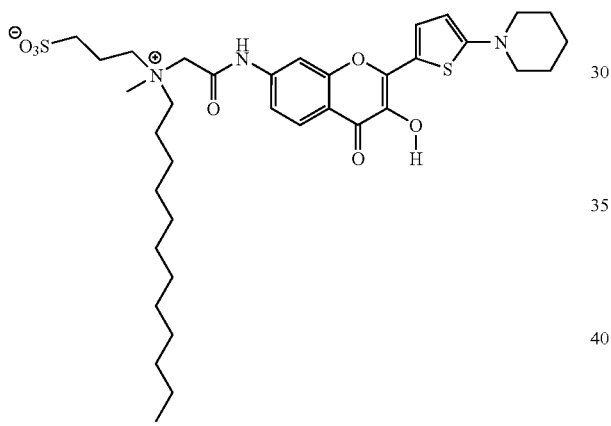

(3)

Compound of Formula (4)

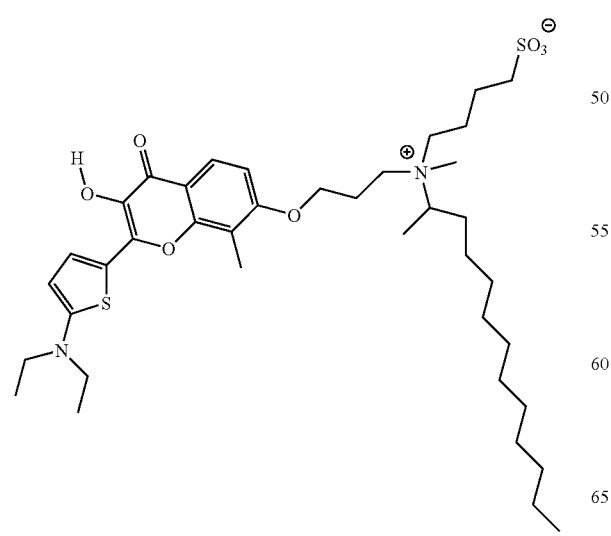

(4)

According to the invention, the compound of formula (2) (1-dodecanaminium, N-[[2-[4-Diethylaminophenyl]-3-hydroxychromon-6-yl]-methyl]-N-methyl-N-(3-sulfopropyl)-, inner salt, "F2N12S") is obtained by a process comprising the steps of:

a) reacting 6-bromomethyl-4'-(diethylamino)-3-hydroxyflavone with dodecylmethylamine to form the corresponding tertiary amine (4'-(diethylamino)-6-(dodecyl (methyl)aminomethyl)-3-hydroxyflavone; and b) reacting with propansultone to form the compound of formula (2).

The compound of formula (3) (1-dodecanaminium, N-[2-[[3-hydroxy-[2-(5-(1-piperidinyl)-2-thienyl]-chromon-6-yl]amino]-2-oxoethyl]-N-methyl-N-(3-sulfopropyl)-, inner salt) may be obtained by the following process, comprising the steps of:

reacting N1-(4-acetyl-3-hydroxyphenyl)acetamide with 5-piperidino-2-thiophenecarbaldehyde in the presence of an alkoxide base, preferably sodium methanoate followed by addition of excess of hydrogen peroxide and an alkoxide base to form N1-[3-hydroxy-2-(5-piperidino-2-thienyl)-7-chromonyl]acetamide;

hydrolysing of N1-[3-hydroxy-2-(5-piperidino-2-thienyl)-7-chromonyl]acetamide in an acid affording 7-amino-3-hydroxy-2-(5-piperidino-2-thienyl)chromone;

reacting the latter with chloroacetylchloride which results in N1-[3-hydroxy-2-(5-piperidino-2-thienyl)-7-chromonyl]-2-chloroacetamide;

reacting the latter with dodecylmethylamine to form corresponding tertiary amine (N1-[3-hydroxy-2-(5-piperidino-2-thienyl)-7-chromonyl]-2-dodecyl(methyl)aminoacetamide, and reacting with propansultone to form compound of formula (3)

The compound of formula (4) (1-dodecanaminium, N-methyl-N-[3-propoxy-[2-[5-Diethylamino-2-thienyl]-3-hydroxy-8-methylchromon-7-yl]]-N-(3-sulfopropyl)-, inner salt, "TCN12S") may be obtained by the following process, comprising the steps of:

reacting 3-methyl-2,4-dihydroxyacetophenone with a base, preferably potassium carbonate, followed by the addition of 1-bromo-3-chloro-propane to form 4-(3-chloropropoxy)-3-methyl-2-hydroxyacetophenone, reacting the latter with N-methyldodecylamine in the presence of a base (preferably potassium carbonate) and iodide (preferably potassium iodide) to form 4-[3-(Dodecylmethylamino)-propoxy]-3-methyl-2-hydroxyacetophenone, reacting the latter with 5-(1-(N,N-diethylamino))-2-thiophenecarbaldehyde in the presence of a base and a peroxide, preferably sodium methoxide and hydrogen peroxide, respectively, to form 2-(5-Diethylaminothiophen-2-yl)-7-[3-(dodecylmethylamino)-propoxy]-8-methyl-3-hydroxychromone, reacting with propansultone to form compound of formula (4).

These compounds could be further purified on silica gel column chromatography.

The compounds of the invention are useful as fluorescent probes for studying cells. Particularly, the compounds according to the invention can be used for studying lipid asymmetry of cell plasma membrane, its surface charge and/or other related structural changes of the plasma membrane. Furthermore, they are useful as fluorescent two band ratiometric probes for detecting changes in the lipid composition of the cell membrane, notably for detecting changes in the lipid distribution between the leaflets of said membrane, because of their peculiar properties. The sensitivity of the probe to said changes of the membranes has been evaluated in lipid vesicles by variation of their lipid composition as well as in living cells by induction of apoptosis with actinomycin D.

Indeed, the compounds of the invention are strongly solvatochromic and electrochromic, and thus very sensitive to the lipid composition and the electrostatic interactions in the membrane. Secondly, the compounds of the invention exhibit two emission bands well separated on the wavelength scale that are differently sensitive to the probe environment. As a consequence, an asymmetry loss in the plasma membrane can be measured from the intensity ratio of the two bands, independently from the local concentration of the probe. Third, the compounds of the invention bind exclusively to the outer leaflet of the cell membrane and do not significantly move to the inner leaflet of the cell interior during the measurements.

The probe TCN12S is an analog of F2N12S and was synthesized to improve the fluorescence properties. Indeed, substitution of the 2-phenyl group with 2-thienyl shifts the absorption maximum from 420 nm to 445 nm, making this probe suitable for excitation with a He/Cd laser (442 nm). Moreover, the resolution between the two emission bands increases from 90 nm (F2N12S) to 120 nm (TCN12S), favoring two-color ratiometric detection.

Thus, the compounds of the invention are used for detecting apoptotic cells, since they present a strong sensitivity to the lipid composition of the bilayers, especially to the presence of the negatively charged lipids phosphatidylglycerol and phosphatidylserine. The compounds of the invention are particularly suitable to sense the anionic lipids that appear during cell apoptosis at the outer leaflet of the plasma membrane.

More particularly, the compounds of the invention are involved in a method for detecting cell apoptosis and a method to assay the cell apoptosis degree.

The method for detecting cell apoptosis according to the invention comprises the following steps:
  i) contacting a compound of the invention with the cells;
  ii) incubating said cells;
  iii) washing the cells; and,
  iv) detecting the apoptotic cells by observing the fluorescence emission spectra of the probe at an excitation wavelength varying from 350 to 500 nm, preferably from 380 to 470 nm and, most preferably at its maximum of absorption (depending on the probe used 420-445 nm), wherein the probe demonstrates a two-band response, one of the bands belonging to the initially excited normal N* form and the other band belonging to the reaction product tautomer T* form.

A higher relative intensity of the short wavelength band is correlated with an increase in the negative surface charge at the outer leaflet of the plasma membrane during apoptosis.

The method to assay cell apoptosis, comprises the following steps:
  i) contacting the compound of the invention with the cells;
  ii) incubating said cells;
  iii) washing the cells; and,
  iv) detecting the changes in the membrane composition of the cells by
    a. collecting the emission spectra of the compound inserted into an apoptotic cell by exiting said compound with an excitation wavelength varying from 350 to 500 nm, preferably from 380 to 470 nm and, most preferably at its maximum of absorption (depending on the probe used 420-445 nm),
    b. selecting the T* band and the N* band in the emission spectra; and,
    c. quantifying the loss of asymmetry of the cell plasma membrane during apoptosis by dividing the intensity of the T* band by the intensity of the N* band.

Preferably, in the above-mentioned methods, the cells are incubated during an elapsed time varying from 5 to 10 minutes.

The selection of the T* band and the N* band in the emission spectra is made by collecting the emission light with two broad-band filters in two spectral regions: at 470 nm-500 nm (blue-green region) to monitor the emission of the N* band and above 585 nm (orange-red region) to collect the emission of the T* band. As mentioned above, the quantification of the loss of asymmetry is obtained by dividing the intensity of the T* band by the intensity of the N* band. A lower ratio of said two bands is correlated with an increased loss of asymmetry of the cell plasma membrane during apoptosis, thus providing information about the degree of the apoptotic transformation.

The proposed method for detecting apoptosis is characterized by the following advantages compared to the commonly used method based on fluorescently labelled annexin V:
  1) The fluorescence ratiometric measurements with the use of a compound according to the invention provide absolute values that are independent of the probe concentration. Therefore, this technique is more precise and allows quantitative estimation of the level of apoptosis.
  2) the method is simple and inexpensive because it is based on use of synthetic organic molecule as a probe.

The present invention also relates to a kit suitable for detecting and/or quantifying and/or isolating apoptotic or necrotic cells comprising the compound according to the invention, optionally conjugated to a reagent. Such a kit is useful not only for research purposes but also in medical or veterinary fields, for example to test the quality of spermatozoa before an artificial fertilization. Examples of reagent that may be used in the kit of the invention include a compound that reports on cell necrosis but does not sense cell apoptosis. Preferably, the reagent is propidium iodide, whose fluorescence intensity increases due to penetration into the nucleus of dead cells.

The kit containing the compound of the invention associated/conjugated to propidium iodide may be used as a probe in cytometry analysis for separating apoptotic, necrotic and living cells.

The present invention also relates to a method for screening compounds that induce or modulate apoptosis. Such a method comprises the following steps:
  i) contacting the compound/drug to be tested with the cells;
  ii) applying the method for detecting cell apoptosis or the method to assay cell apoptosis according to the invention;
  iii) comparing the results with those obtained with a control (cells that were not in contact with the compound/drug to be tested).

The present invention further relates to a method for following the evolution of a patient's disease, said disease involving the apoptosis of cells, by applying, to a patient sample, the method for detecting cell apoptosis and/or the method to assay the cell apoptosis degree. Advantageously, said method is used to follow the evolution of diseases such as Alzheimer, Parkinson, heart failure and cancers.

The following examples illustrate the invention.

SHORT DESCRIPTION OF THE FIGURES

FIG. 1: (a) Formula and location of 3-HF probes of the prior art F and F2N8 and of the probe of the invention F2N12S in phospholipid bilayers (a). Confocal fluorescence images of L 929 cells stained with probes F (b), F2N8 (c) and F2N12S (d). All images were obtained by collecting fluorescence in the 585-700 nm wavelength range 10 min after probe addition. Scale bar, 10 μm (b).

Figure 2:
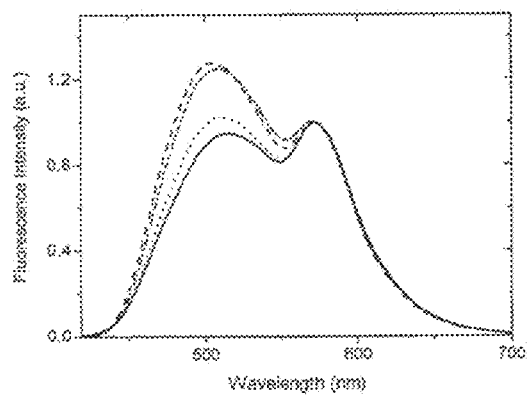

FIG. 2: Fluorescence response in the emission spectra of F2N12S to variation of liposome composition: EYPC (solid line), EYPE (dot line), EYPG (dash dot line) and BBPS (dash line). The spectra were excited at 400 nm. Final probe concentration was 0.1 μM.

Figure 3:
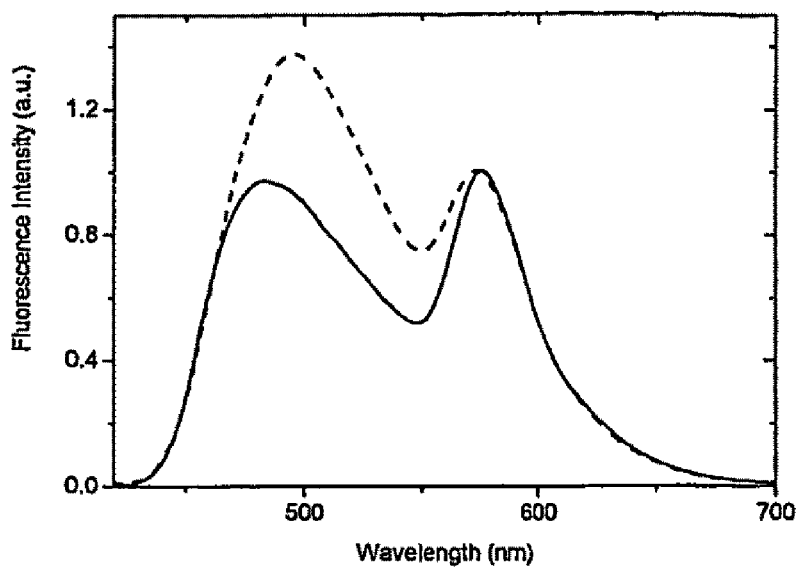

FIG. 3: Emission spectra of the probe F2N12S in living (solid line) and apoptotic (dash line) CEM cells. Excitation wavelength was 400 nm. Final probe concentration was 0.1 μM.

Figure 4:
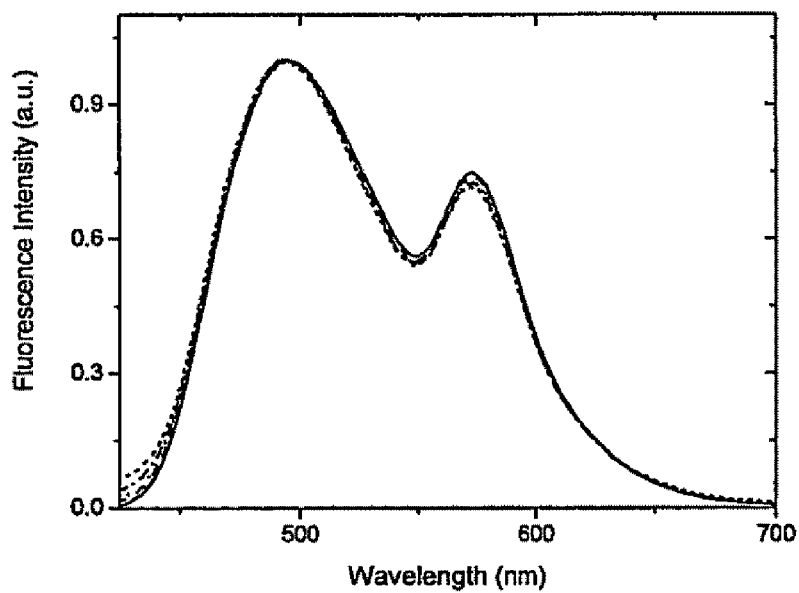

FIG. 4: $Ca^{2+}$ dependence of F2N12S emission spectra in apoptotic CEM cells. The excitation wavelength was 400 nm. The spectra were recorded at $Ca^{2+}$ concentrations of 0.2, 0.4, 0.8, 1.2 and 2 mM and normalized. Final probe concentration was 0.1 μM.

Figure 5:
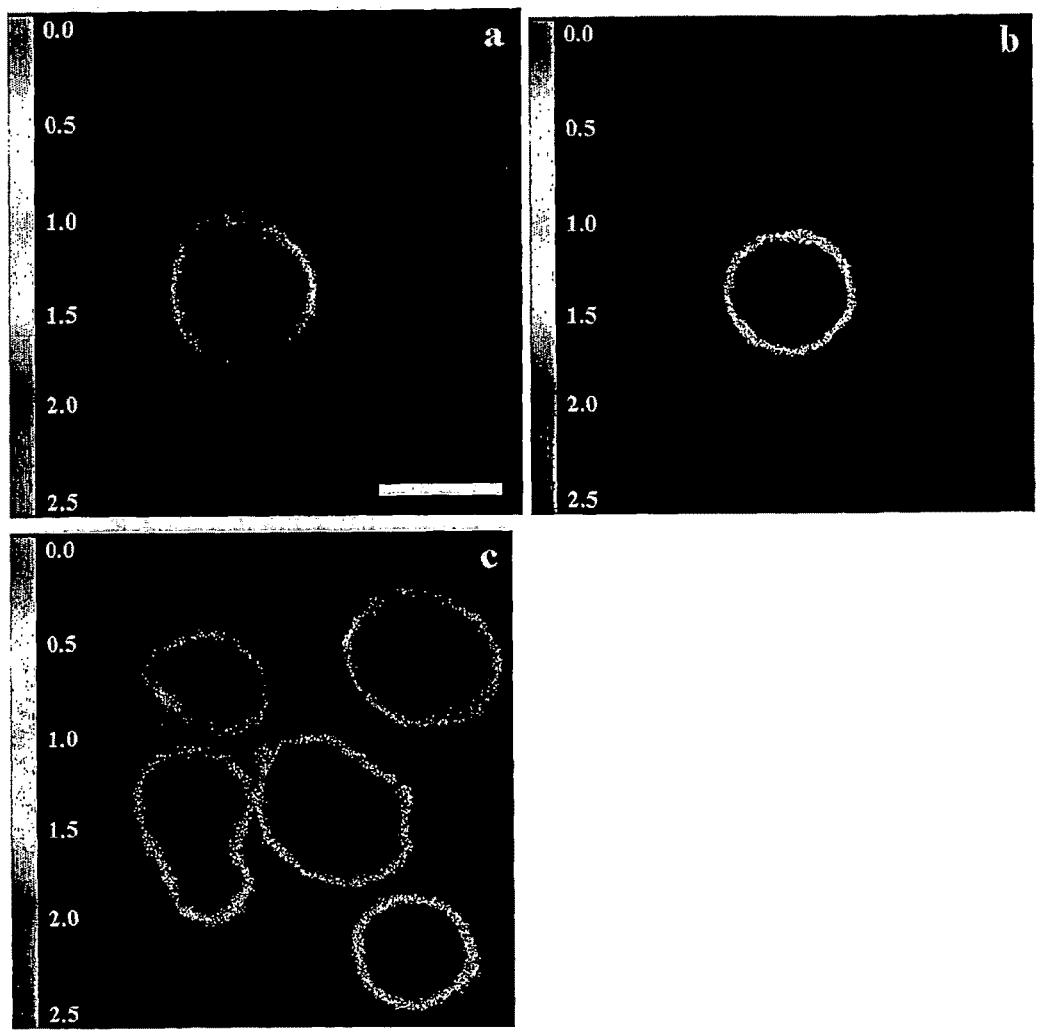

FIG. 5: Confocal fluorescence ratiometric images of CEM cells stained with F2N12S: normal cells (a); apoptotic cells, obtained by FITC-annexin based sorting of cells treated with actinomycin (b); and actinomycin-treated without cell sorting (c). The images were recorded after a 10 min incubation of the probe with the cells. Scale bar, 10 μm.

FIG. 6: Flow cytometry analysis of T lymphoblastoid cells treated by actinomycin D. Cells were stained by annexin V-FITC, PI and F2N12S. In (a), Annexin V-FITC and PI were selectively excited at 488 nm. Cells are sorted into living, dead and apoptotic cell populations. In (b), F2N12S is selectively excited at 407 nm. Living cells are discriminated from apoptotic and necrotic cells. In (c), the PI fluorescence intensities are plotted versus the T*/N* ratio of F2N12S. Living cells are in green, apoptotic cells are in cyan and dead cells are in orange. In (d), the populations sorted using the F2N12S/PI couple were colored according to their response with the annexin V/PI couple. The wavelengths of maximal transmission and bandwidths of used filters are indicated in brackets.

Figure 6A:
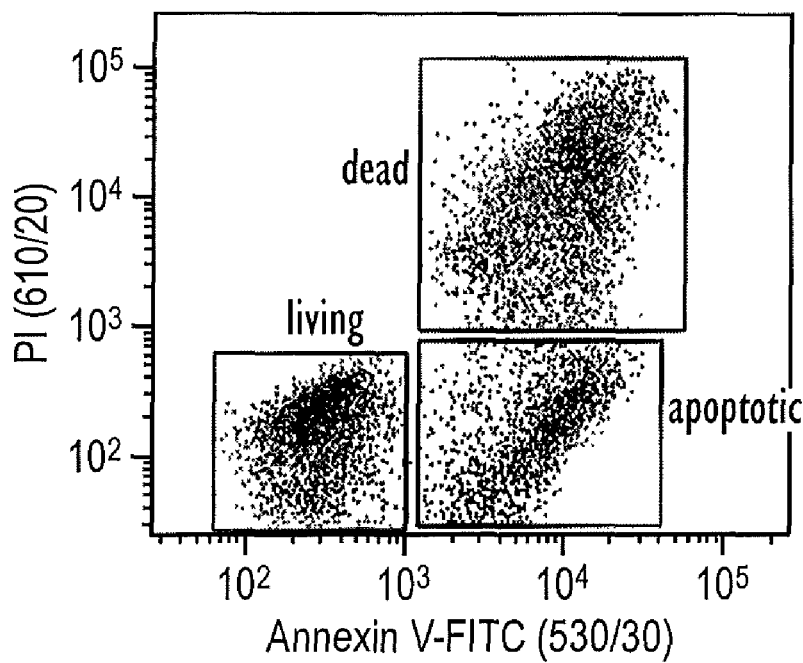
Figure 6B:
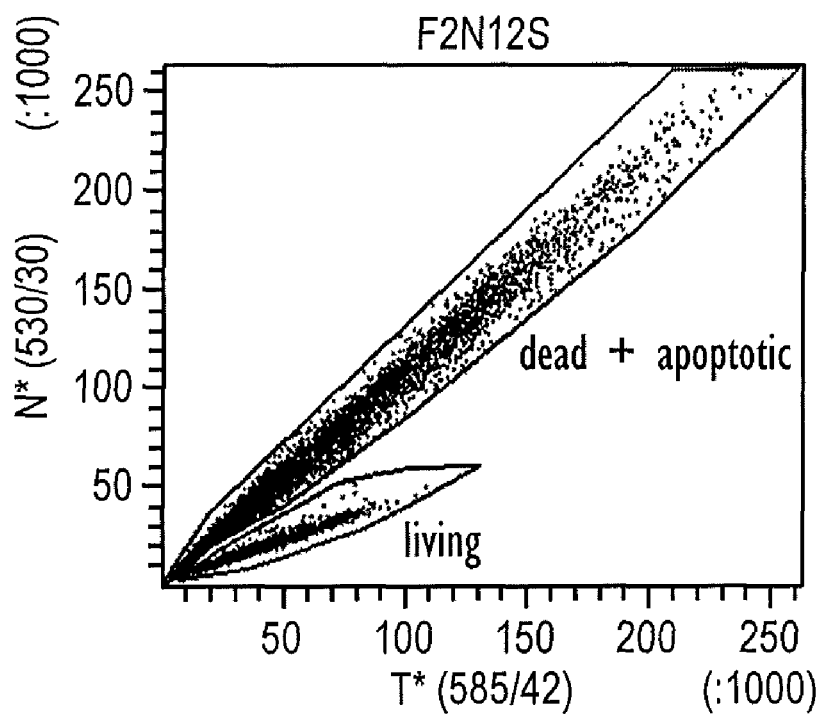
Figure 6C:
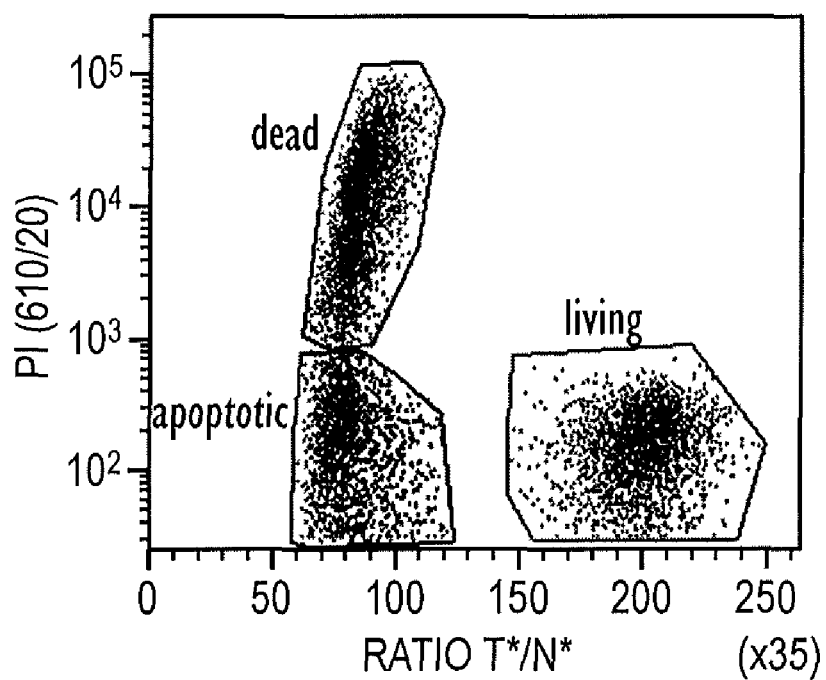
Figure 6D:
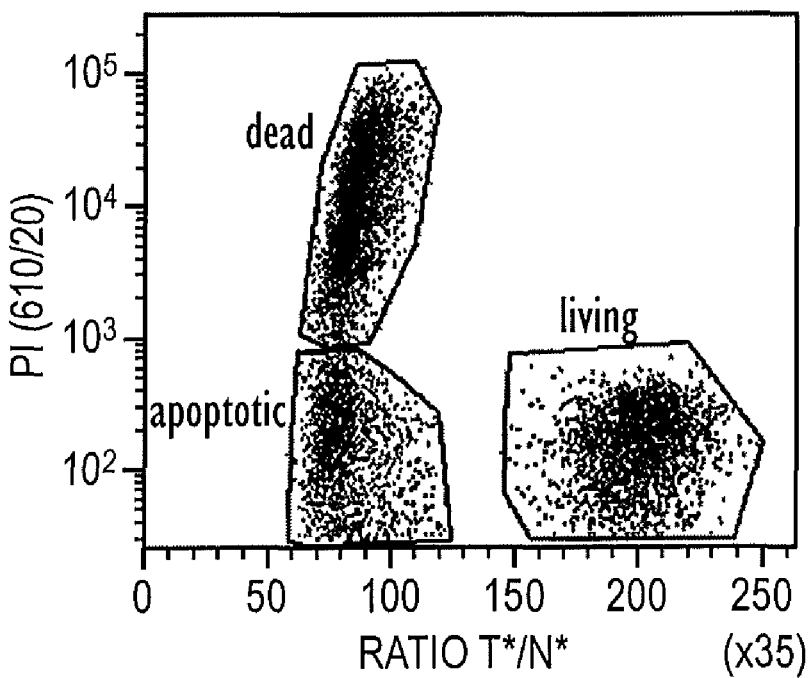
Figure 7:
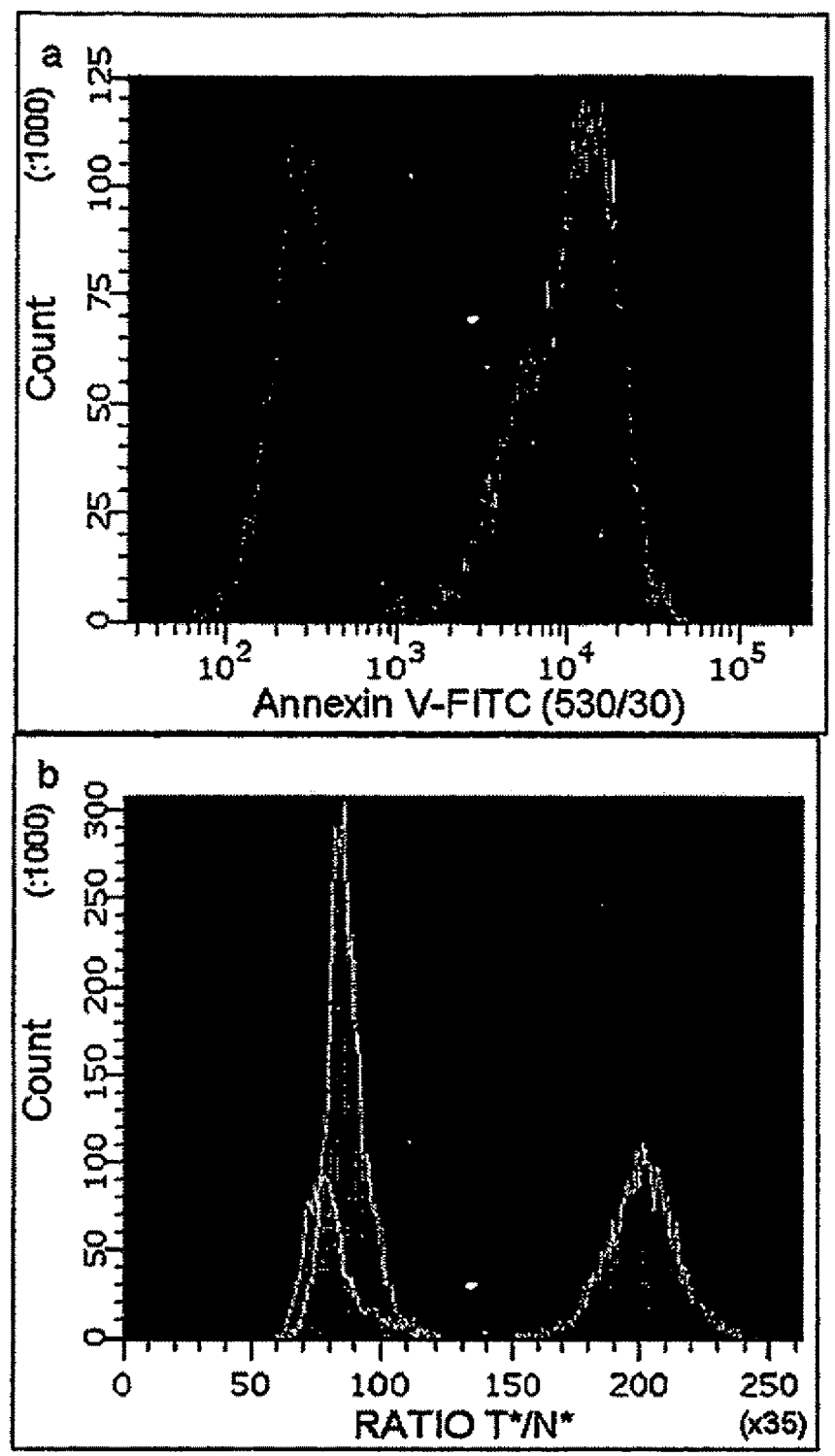

FIG. 7: Comparison of the intensiometric response of annexin V-FITC (a) with the ratiometric fluorescence response of F2N12S (b). Living, dead and apoptotic cells were identified as described in FIG. 6, by using either the annexin V-FITC/PI (a) or the F2N12S/PI (b) couple of dyes.

Figure 8:
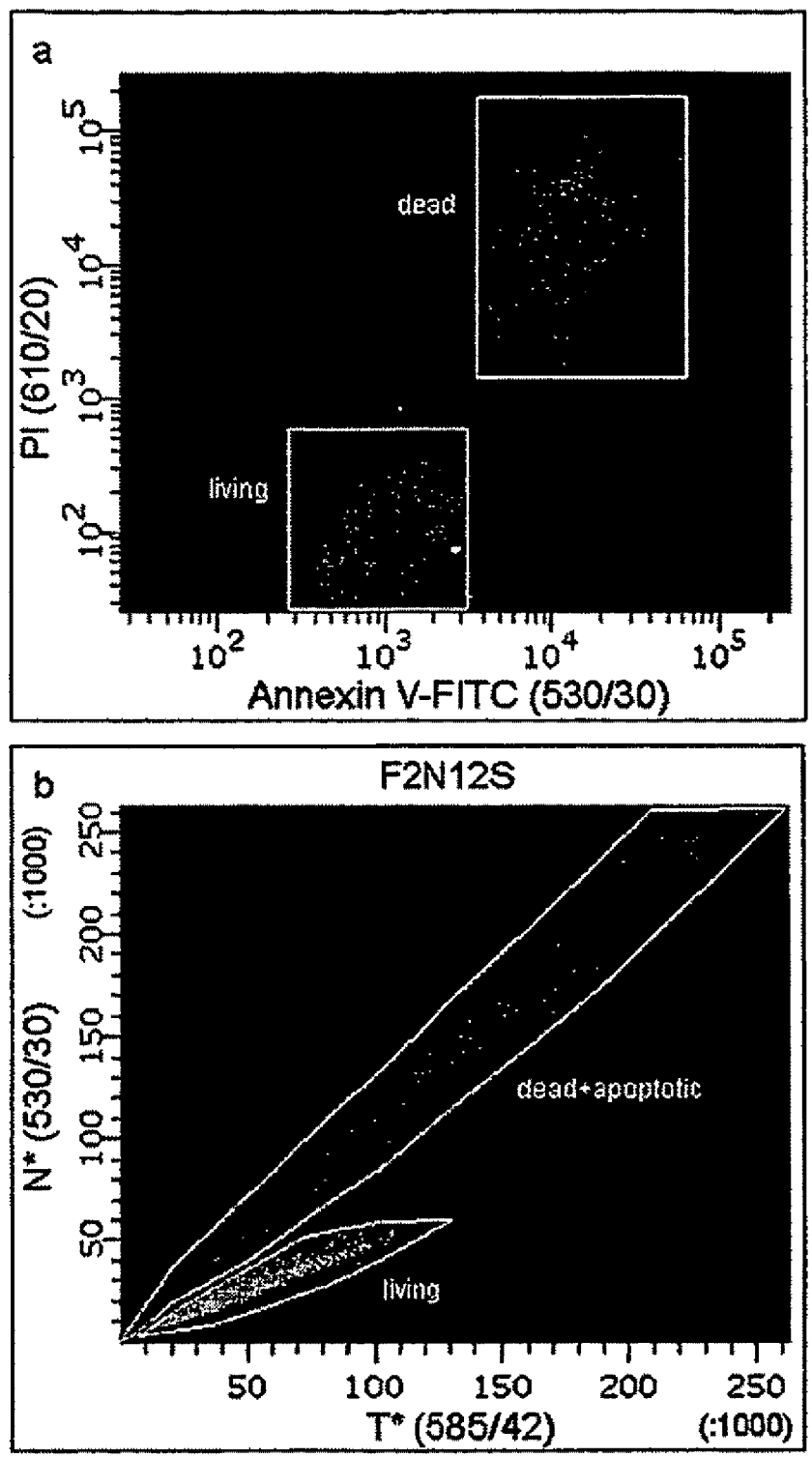

FIG. 8: Comparison of the response of annexin V-FITC and F2N12S on non-treated T lymphoblastoid cells stained by annexin V-FITC, PI and F2N12S. In (a), annexin V-FITC and PI were selectively excited at 488 nm. In (b), F2N12S is selectively excited at 407 nm. Cells are sorted into living and dead cell populations.

Figure 9:
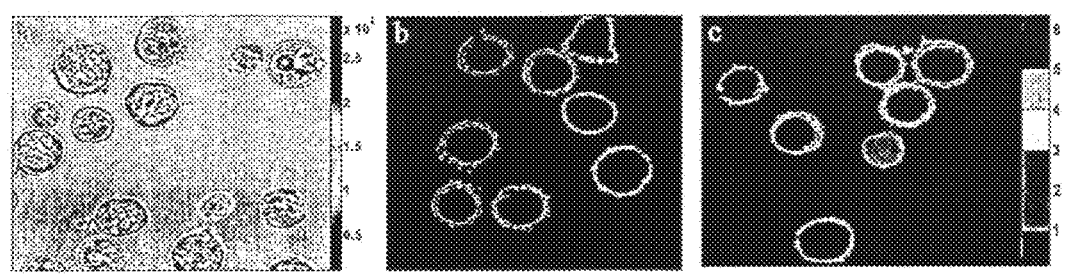

FIG. 9: Laser scanning confocal imaging of T lymphocytes stained with annexin V-FITC (a) and F2N12S (b and c). Combination of transmission and fluorescence images of cells treated with actinomycin D for 18 hours (please complete this sentence). FITC intensity is displayed in pseudocolor by using the color code on the right scale. Due to their low binding to annexin V, normal cells are not visualized in the fluorescence images. (b and c) Ratiometric images of normal (b) and actinomycin D-treated (c) cells stained with 0.2 μM F2N12S. The ratios of intensities of the two bands T*/N* are displayed in pseudocolor by using the color code on the right scale. The size of the images is 60×73.1 μm.

Figure 10:
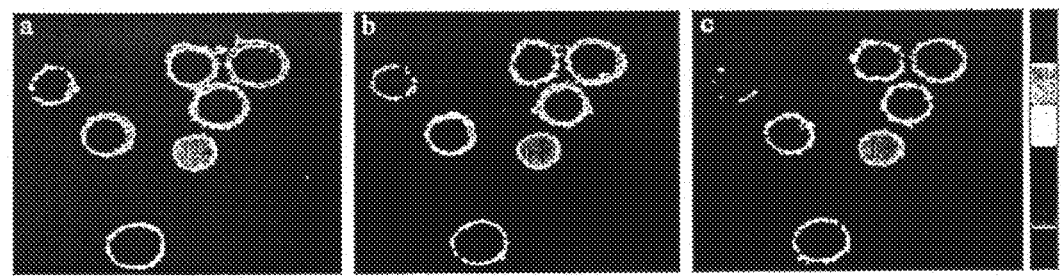

FIG. 10: Time-series of confocal fluorescence ratiometric images of actinomycin D-treated T lymphocytes stained with F2N12S. The cells were treated with actinomycin D for 18 hours and then, incubated with the probe (0.2 μM) for 5 min. Images were recorded at 1 min (a), 10 min (b) and 20 min (c) post incubation. Ratios of intensities are displayed as in FIG. 9. The size of the images is 60×73.1 μm.

MATERIALS AND METHODS

Materials

Actinomycin D, propidium iodide (PI) and type I-A RNAse A: from Sigma Chemical Co. (St. Louis, Mo.).

HBSS: from Gibco.

Annexin V-FITC (Fluorescein IsoThioCyanate) Kit: from Immunotech.

Synthesis of 3-hydroxyflavone Probes

3-HF Probes of the prior art F and F2N8 were synthesized according to the method of preparation described in Ormson, S. M., et al. (Switching Between Charge-Transfer and Proton-Transfer Emission in the Excited-State of A Substituted 3-Hydroxyflavone. J. Photochem. Photobiol. A: Chem., 1994. 81: p. 65-72).

The 3-HF probe of the invention F2N12S, having the formula (2) was synthesized using the following procedure: primarily, 0.1 g of 6-bromomethyl-4'-N,N-diethylamino-3-hydroxyflavone was reacted with 0.2 ml of dodecylmethylamine in 3 ml of dry THF at room temperature for 3 h. After rotor evaporation, the crude product (sufficiently pure according to thin layer chromatography) was dissolved in 2 ml of toluene and 50 μl of dimethylformamide followed by addition of 45 μl of propansultone. The reaction mixture was refluxed for 20 h. After cooling the mixture was diluted with hexane and the product F2N12S was filtered. Purification of F2N12S was done on silica gel column chromatography (dichloromethane/methanol, 4/1, v/v). Yield 40%; UV max in acetonitrile 416 nm, ε=34,000 l×mol-1×cm-1; 1H NMR (300 MHz, CDCl3) 0.86 (3H, t, J 5.80 Hz), 1.16 (6H, t, J 6.8 Hz), 1.2-1.3 (20H, multiplet), 1.75 (2H, m), 2.13 (2H, m), 2.94 (3H, s), 3.10-3.30 (2H, m), 3.40-3.60 (6H, multiplet), 4.70 (2H, s), 6.84 (2H, d, J 8.1 Hz), 7.84 (1H, d, J 8.4 Hz), 7.91 (1H, d, J 8.4), 8.13 (2H, d, J 8.1 Hz), 8.33 (1H, s); MS (FAB) m/z 642.4 (M+).

Cell Culture and Induction of Apoptosis.

Human lymphoid CEM T cells were cultured in X-vivo 15 medium (Cambrex, France) at 37° C. in humidified 5% CO2 atmosphere. Cell viability was checked by trypan blue exclusion. Cells were seeded at $5\times10^5$ cells/ml in the presence or absence of actinomycin D (0.5 μg/ml) for 18 h. Cells were pelleted by centrifugation at 1500 rpm for 5 min and resuspended at $1\times10^6$ cells/ml in X-vivo 15 medium for experiments.

Determination of Hypodiploid DNA

To verify the proportion of apoptotic cells, measurements of hypodiploid DNA with PI by flow cytometry have been performed. After apoptotic treatment, cells were harvested and numbered. Concentration in a 70% ethanol solution in H2O was adjusted to 5×105 cells/ml and fixation was allowed to proceed for at least 1 h at 4° C. Cells were washed once in Hank's balanced salt solution (HBSS) before resuspension in HBSS containing RNAse (0.5 mg/ml), PI (0.1 mg/ml) and incubation for 15 min at room temperature in the dark. Samples were analysed by flow cytometry using the CELLQuest software (Becton Dickinson, San Jose, Calif.). Under these conditions, the content of hypodiploid DNA in CEM T cells was 30±2% (mean±SEM).

Cell Preparation

The cells were washed twice by HBSS before each experiment to eliminate fetal bovine serum. In sorting experiments, cells were resuspended in the binding buffer and labeled with the annexin V-FITC kit. For fluorescence measurements with the probe of the invention F2N12S (fluorometry, flow cytometry and confocal microscopy), cells were resuspended in HBSS with 0.1 µM F2N12S. Then, the cell suspension was placed in a shaker bath for 10 min in the incubator. The staining pattern of the cells was checked with a Confocal Imaging System MRC-1024 (BioRad) to ascertain that fluorescence originates from the plasma membrane.

Flow Cytometry

Cells treated for induction of apoptosis by actinomycin D as described above were sorted into living, apoptotic and dead cells using FITC-labeled annexinV and propidium iodide (PI) with a FACStar+cell sorter (BD Biosciences, CA, USA) equipped with an argon laser (488 nm) and emission filters DF30 and DF22 centered at 530 nm and 630 nm, respectively. The populations of sorted cells were used for subsequent fluorescent analysis with the new dye.

For the validation of F2N12S in cell cytometry, we used a FASCARIA™ (cell sorter) (BD Biosciences, CA, USA) equipped with an argon laser (488 nm) and a diode laser (407 nm) and emission filters DF30, DF42 and DF20 centered at 530 nm, 585 nm and 610 nm, respectively. The optical pathways corresponding to the argon laser and to the diode laser are independent. Data were analyzed using the FACSDIVA™ (cell sorter) Software (BD Biosciences). The granulation, size and fluorescence intensity were recorded at a rate of ~1000 cells per second.

Toxicity Test

The toxicity of the F2N12S molecules was tested by flow cytometry using PI (19 µM). Cells were washed twice as described above and separated in nine batches: three batches for control measurements, three batches with 10-7 M F2N12S and three batches with 10-6 M F2N12S. The batches were incubated for 0.5 hour, 1 hour and 4 hours, respectively. The 488 nm line of an argon laser was used as the excitation light source. Emission was collected by using the 630FD22 filter.

Spectroscopic Measurements

Fluorescence spectra were recorded on a FLUOROMAX-3® (spectrofluorometer) (JobinYvon Horiba). The excitation wavelength for fluorescence emission spectra of F2N12S probes was 400 nm. All spectra were corrected for lamp intensity variations and signals from the blank.

Fluorescence Imaging

For collecting cell images, a Laser Scanning Confocal Imaging System MRC-1024 (Bio-Rad) was used. Cells in chambered cover glass were prepared by following the preparation procedure described above. The 442 nm line of a HeCd laser was used as the excitation light source. Emission was collected by using two filters: 485/30 for the N* band and 585LP for the T* band. Collected images were analyzed by the Amira 3.0 software.

EXAMPLES

Example 1

Development of a New Probe with High Selectivity to Cell Plasma Membranes and Drastic Sensitivity to Surface Potential Confocal laser microscopy have been performed on adherent L 929 cells stained with these first generation molecules (FIG. 1.*b, c*). The obtained fluorescence images reveal a rapid penetration of these dyes inside the cells.

Images of adherent L 929 cells stained with probes F2N12S (FIG. 1.*d*) demonstrate emission exclusively from the plasma membranes. The probes stay in the membrane during the whole observation time under the microscope, which is limited by the lifetime of the cells in HBSS buffer (approx. 1 hour). Moreover, F2N12S probe was found to be of sufficient brightness for fluorescence microscopy of individual cells. Some inhomogeneity in the distribution of the fluorescence intensity at the plasma membrane has been observed. This is probably connected with the heterogeneous lipid distribution in the bilayer that affects the probe distribution.

Next, the cytotoxicity of the newly synthesized probe, F2N12S, was evaluated on the human lymphoid cell line CEM T. F2N12S was added at 0.1 µM (working concentration) and 1 µM and, incubated for different times (0.5, 1 and 4 hours). No cytotoxicity was observed with 0.1 µM F2N12S even for a 4 h incubation time. Even with a 1 µM concentration, the cytotoxicity of F2N12S was very limited, since the percentage of dead cells did not exceed 4%.

Example 2

Effect of Surface Potential on F2N12S Fluorescence

To model the increase in the negative surface charge at the outer leaflet of the plasma membrane during apoptosis, large unilamellar vesicles (LUV) composed of neutral (phosphatidylcholine PC and phosphatidylethanolamine PE) and negatively charged (phosphatidylglycerol PG) and phosphatidylserine PS) phospholipids have been used. The probe of the invention F2N12S demonstrates strong two-band response to the surface charge in large unilamellar vesicles (LUV). Indeed, in anionic vesicles (PG and PS) this probe shows a higher relative intensity of the short-wavelength band as compared to neutral PC vesicles (FIG. 2). A significantly smaller increase in the short-wavelength band relative intensity is observed also for neutral PE vesicles.

Example 3

Response of F2N12S to Apoptosis in Cell Suspensions and $Ca^{2+}$-Dependence of this Response CEM T cells apoptosis was induced by actinomycin D, an inhibitor of DNA-primed RNA polymerase. Then, apoptotic cells were separated from living cells by cytometry using the FITC-annexin marker. Next, the living and apoptotic cells were labeled with F2N12S and their emission spectra were recorded at an excitation wavelength of 400 nm. At this wavelength, the excitation of FITC is minimal and its residual emission was subtracted from the emission spectrum of F2N12S. The results are presented on FIG. 3. Apoptosis results in dramatic changes of the fluorescence spectrum of probe F2N12S since the relative intensity of the short-wavelength band is nearly 2-fold higher than that in living cells. This result is in line with the model experiments on the surface charge effect in lipid vesicles of example 2 (FIG. 2). In living cells, the separation of the two bands of F2N12S is significantly larger than that in lipid vesicles. The dependence of F2N12S response to the concentration of Ca2+ in the medium has been tested (FIG. 4). The results show that the response of F2N12S in apoptotic cells is insensitive to $Ca^{2+}$ in the concentration range 0-2 mM. This independence on $Ca^{2+}$ concentration is a significant advantage over the commonly used methodology based on annexin V.

Example 4

Ratiometric Imaging of Normal and Apoptotic Cells

Two-color confocal fluorescence microscopy of CEM T cells stained with F2N12S was performed. Emission light was collected in two spectral regions: at 470-500 nm to monitor the emission of the N* band and above 585 nm to collect the emission of the T* band. Ratiometric images were obtained by dividing the intensity of the T* band by the intensity of the N* band and were used to monitor the cell plasma membrane changes induced by addition of actinomycin D (FIG. 5, a-c). The ratios of intensities of the T* band to those of the N* band are displayed in pseudocolor by using the color code on the left scale.

F2N12S probes provide strong and well-detectable ratiometric response to the changes of membrane asymmetry on a single cell level.

In non-treated cells (FIG. 5 a), the fluorescence intensity ratio at the plasma membrane is close to 1, as expected from fluorescence measurements in cell suspensions (FIG. 3). In apoptotic CEM T cells (obtained by cell sorting), the emission ratio of the dye from plasma membrane is very different, being around 0.25 on the average (FIG. 5 b). This 4-fold change in the ratio is even higher than that observed in cell suspensions.

Fluorescence ratiometric imaging of cells treated with actinomycin D but not sorted by cytometry (FIG. 5 c) have been performed. A strong heterogeneity of the fluorescence ratio on the cell membranes can be observed. In FIG. 5 c, the living cells in green pseudo color (ratio close to 1) could be easily distinguished from the apoptotic cells in red pseudo color (ratio close to 0.25). Cells with an intensity ratio between 0.25 and 1 are also observed. In those cells, the apoptotic process may be on an intermediate state. These cells are characterized by a strong heterogeneity of the ratio (color) distribution, which can be connected with different levels of membrane asymmetry at different parts of the plasma membranes during of apoptosis. Thus, the method to assay the apoptosis degree allows not only detection of apoptosis but also provides information about the degree of the apoptotic transformation of the cell membranes as well as on the spatial and kinetic evolution of this transformation.

Example 5

Validation of F2N12S in Flow Cytometry Analysis

T lymphoblastoid cells were treated with actinomycin D and labeled simultaneously by FITC-labeled annexin V, propidium iodide (PI) and F2N12S. Selective excitation of FITC and PI was obtained at 488 nm, a wavelength where F2N12S does not absorb. The emissions of FITC and PI were collected in the spectral regions of 515-545 nm and 600-620 nm, respectively. The bi-parametric representation of the fluorescence intensities (PI versus FITC) shows three distinct populations, i) viable cells which have low FITC and PI signals, ii) apoptotic cells which have high FITC and low PI signals, and iii) dead cells which exhibit both high FITC and PI signals due to disruption of cellular membrane integrity (FIG. 6a). The percentage of living, apoptotic and dead cells were found to be 33, 18 and 49% respectively. Selective excitation of F2N12S on the same cells was achieved with a second laser source at 407 nm. The emission light in this case was collected in two spectral regions: at 515-545 nm to monitor the emission of the N* band and 564-606 nm to collect the emission of the T* band (FIG. 6b). The bi-parametric representation of F2N12S data (N* band versus T* band intensities at 530 and 585 nm) (FIG. 6b) clearly shows two populations. The first one exhibits a low N*/T* intensity ratio and can be assigned to living cells according to our spectroscopic data. The second one is characterized by a high N*/T* intensity ratio (shown in red) and can be assigned to apoptotic and dead cells. Noticeably, when probe F2N12S was used without annexin V-FITC and PI, the T*/N* ratios were very close to those observed in the triple staining procedure, indicating that in our cytometry experiments, the fluorescence signal of F2N12S dye is not polluted with the fluorescence of the other two dyes.

The probe of the invention F2N12S has been combined with PI and the fluorescence intensities of PI have been represented as a function of the T*/N* ratio of F2N12S (FIG. 6c). In this case, the populations of apoptotic and dead cells are clearly discriminated by using the differences in the PI intensities. Interestingly, the percentages of living, apoptotic and dead cells were found to be 32.5, 19.5 and 48% respectively and thus closely matched those obtained with annexin V-FITC/PI. This conclusion was further strengthened when the populations discriminated by the F2N12S/PI couple were colored according to their response with the annexin V-FITC/PI couple (FIG. 6d). Comparison of FIG. 6d with FIG. 6c shows a very good overlap between the populations identified by the two couples of dyes, validating the use of F2N12S/PI in cell sorting. Moreover, very similar F2N12S intensity ratio values were obtained when T lymphoblastoid cells were substituted by 3T3 fibroblasts or HeLa cells (data not shown), indicating that the F2N12S response is general and not specific to a given cell line.

To further compare the two couples of dyes, the distribution of the single-wavelength intensity values for annexin V-FITC (FIG. 7a) was compared with the distribution of the two-band intensity ratio values of probe F2N12S (FIG. 7b). The relative standard deviations for living, apoptotic and dead cells are respectively 0.84, 1.06 and 1.17 in (a) and 0.14, 0.21 and 0.16 in (b). Then, for all three cell populations, the dispersions of the distributions were found to be much narrower for F2N12S than for annexin V-FITC, enabling a more accurate separation of the populations, especially between living and non living cells.

In a next step, the response of F2N12S (FIG. 8b) was compared with the response of the annexin V-FITC/PI couple (FIG. 8a) on non-treated T lymphoblastoid cells (FIG. 8). Two distinct populations of living and dead cells could be easily discriminated in both cases with the same percentage of dead cells (5%). This indicates that F2N12S alone can be used to control the percentage of dead cells in non-treated cell populations.

Taken together, the data show that cells can be sorted by F2N12S/PI to provide the subpopulations of necrotic, apoptotic and living cells with improved separation, simpler preparation protocol, and less precaution than with the annexin V-FITC/PI couple.

Example 6

Application of F2N12S in Confocal Microscopy

To further compare F2N12S and annexinV-derived probes, two-color ratiometric images of F2N12S-labeled cells undergoing apoptosis were recorded by laser scanning confocal microscopy and compared with intensity based images obtained using annexin V-FITC. Since annexin V-FITC labels only apoptotic and necrotic cells, it does not visualize normal cells in fluorescence images (FIG. 9a). Moreover, the fluorescence intensity of apoptotic cells varies considerably from cell to cell. These differences are difficult to interpret since the intensity depends on the probe concentration as well as on the size and confluence of the cells. In contrast to annexin V-FITC, F2N12S stains both normal (FIG. 9b) and apoptotic cells (FIG. 9c) but in different colors. Normal cells stained with F2N12S exhibit intensity ratios between 4 and 6. Cells treated with actinomycin D exhibit more heterogeneous intensity ratios (FIG. 9c) since cells with ratios close to 5, corresponding to normal cells, are observed together with cells that exhibit much lower T*/N* intensity ratios, between 1 and 2. According to our spectroscopy and flow cytometry data, the latter cells are apoptotic. Interestingly, cells with intermediate ratios between 2 and 4 are also observed and correspond to cells on the initial steps of apoptosis. This indicates that the probes according to the invention can not only identify apoptotic cells, but also quantify the level of their apoptotic transformation. Thus, unlike annexin V-FITC, these probes provide an absolute parameter, the intensity ratio, which can be calibrated, and can characterize the level of apoptosis independently of the probe/cell concentration and the excitation light intensity. In addition, the inventors have observed that in normal cells and cells on the initial steps of apoptosis, the T*/N* intensity ratio is not evenly distributed within the plasma membrane of a given cell. This may indicate an inhomogeneous lipid composition of their plasma membranes that is likely related to the presence of lipid domains.

The inventors also follow apoptotic transformation of the plasma membrane as a function of time. Normal and actinomycin D-treated cells were stained with the corresponding probe and the fluorescence images were subsequently recorded during 20 min. When annexin V-FITC was used, it was not possible to detect any time-dependent changes both in normal and apoptotic cells. Using F2N12S, it was observed that actinomycin D-treated cells exhibit relatively fast change in the emission color of their membranes (FIG. 10), while normal cells do not show significant color change within the same time period. The color of the cells changes from blue-green to orange-red, indicating the evolution of the apoptotic process that occurs within 20 min.

In conclusion, the most important advantage of the probes according to the invention relies on its fluorescence ratiometric response to apoptosis. This ratiometric response provides a self-calibrating absolute parameter of apoptotic transformation, which does not depend on the probe concentration or on instrumental factors, such as fluctuations of light source intensity or sensitivity of the detector. In this respect, these probes are especially interesting for two-color ratiometric confocal imaging using a single excitation light source. Using these probes, the degree, the spatial distribution and the kinetics of the apoptotic changes over the cell plasma membranes can be sensitively monitored.

Example 7

Synthesis of Probe TCN12S 4-(3-Chloropropoxy)-3-methyl-2-hydroxyacetophenone 3-methyl-2,4-dihydroxyacetophenone (0.3 g) and potassium carbonate (0.5 g) were refluxed for 30 min in acetone. Then, the flask was cooled and 1-bromo-3-chloro-propane (0.3 ml) was added. Then, the mixture was refluxed for 24 hours. The product was purified on column chromatography by using ethyl acetate/heptane as an eluent (EtOAc/Hept=20/80). Yield 82%.

4-[3-(Dodecylmethylamino)-propoxy]-3-methyl-2-hydroxyacetophenone

A mixture of 4-(3-Chloropropoxy)-3-methyl-2-hydroxyacetophenone (0.1 g), N-methyldodecylamine (0.5 ml), potassium carbonate (0.5 g) and potassium iodide (0.1 g) was refluxed in butanone for 48 hours. The product was purified on column chromatography by using ethyl acetate/heptane as an eluent (EtOAc/Hept=60/40). Yield 72%.

2-(5-Diethylaminothiophen-2-yl)-7-[3-(dodecylmethylamino)-propoxy]-8-methyl-3-hydroxychromone 4-[3-(Dodecylmethylamino)-propoxy]-3-methyl-2-hydroxyacetophenone (0.4 g) and 5-(1-(N,N-diethylamino))-2-thiophenecarbaldehyde (0.2 g) were dissolved in a minimum volume of DMF followed by NaOMe (0.2 g). After the mixture was stirred overnight, it was diluted with ethanol and then, subsequently, 1.5 g of sodium methoxide and 1.5 ml of 30% hydrogen peroxide were added. The mixture was refluxed for 3 min, cooled to room temperature and poured into water. After neutralization with diluted HCl, the resultant precipitate was filtered and the product was purified on column chromatography by using ethyl acetate/heptane as eluent (EtOAc/Hept=20/80). Yield 30%.

Probe TCN12S

Hydroxychromone 4 (60 mg) was dissolved in acetonitrile followed by addition of propansultone (30 µl). The mixture was refluxed for 24 h. Then the solvent was evaporated and the purification of the product was done on silica gel chromatography by using dichloromethane/methanol mixture as eluent (CH$_2$Cl$_2$/MeOH=90/10). Yield 70%.

$^1$H NMR (300 MHz, CDCl$_3$) 0.89 (3H, t, J 5.80 Hz), 1.2-1.3 (26H, m), 1.75 (2H, m) 2.05 (2H, m), 2.3 (3H, s), 2.44 (2H, m), 2.9 (2H, m), 3.12 (3H, s), 3.20-3.30 (6H, m), 3.48 (2H, m), 3.76 (2H, m), 3.9-4.1 (2H, m), 6.03 (1H, bs), 6.81 (1H, bs), 7.72 (2H, bs).

The invention claimed is:

1. A compound of formula (1)

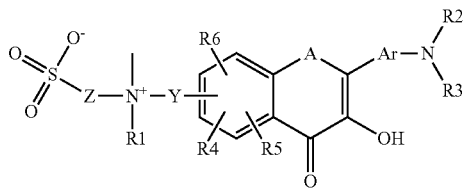

wherein:

R1 is a linear alkyl group of 4 to 20 carbon atoms;

Y is a linear alkyl group of 1 to 5 carbon atoms or a group of formula —R—O—R'—, —R—CO—R'— or —R—CO—NH—R'—, in which R is a linear alkyl group of 1 to 3 carbon atoms, R' is a linear alkylene group of 0-3 carbon atoms, Y being linked to the bicycle in position 6 or 7;

Z is a linear alkyl chain of 3 or 4 carbon atoms;

A is an oxygen atom, a sulphur atom, or a —NH group, or an aminoalkyl group —NR" in which R" is an alkyl group of 1 to 20 carbon atoms;

Ar is an aromatic cycle or polycycle consisting of 6 to 14 carbon atoms, or an aromatic heterocycle, said heterocycle containing 4, 5 or 6 carbon atoms and at least one heteroatom selected from the group consisting of N, S, and O, or a condensed aromatic heterobicycle, said heterobicycle consisting of 6 to 9 carbon atoms and at least one heteroatom selected in the group consisting of N, S, and O;

R2 and R3, which are identical or different, each is a hydrogen atom or an alkyl group of 1 to 4 carbon atoms, R2 and R3 optionally forming a 5- to 7-membered ring with the nitrogen atom;

R4, R5 and R6, identical or different, is a hydrogen, a linear alkyl group or a linear oxyalkyl group of 1 to 4 carbon atoms.

2. The compound according to claim 1, wherein A is selected from the group consisting of an oxygen atom, a sulphur atom, or a —NH group.

3. The compound according to claim 1, wherein Ar is selected from the group consisting of phenyl, naphthyl, furfuryl, benzofurfuryl, isobenzofurfuryl, pyrrolyl, indolyl, isoindolyl, indolizinyl, thienyl, benzothienyl, oxazolyl, pyrazolyl, thiazolyl, imidazolyl, triazolyl, pyridyl, quinolyl, isoquinolyl, phtalazinyl, naphthyridinyl, quinoxalinyl, quinazolinyl, cinnolinyl, pteridinyl, pyrazinyl, pyrimidinyl, purinyl, thieno[3,2-b]thiophene.

4. The compound according to claim 3, wherein Ar is selected from the group consisting of phenyl, naphthyl, furfuryl, benzofurfuryl, isobenzofurfuryl, pyrrolyl, indolyl, isoindolyl, indolizinyl, thienyl, benzothienyl, pyrazinyl, pyrimidinyl.

5. The compound according to claim 4, wherein Ar is selected from the group consisting of phenyl and thienyl.

6. The compound according to claim 5, having the specific formula (2):

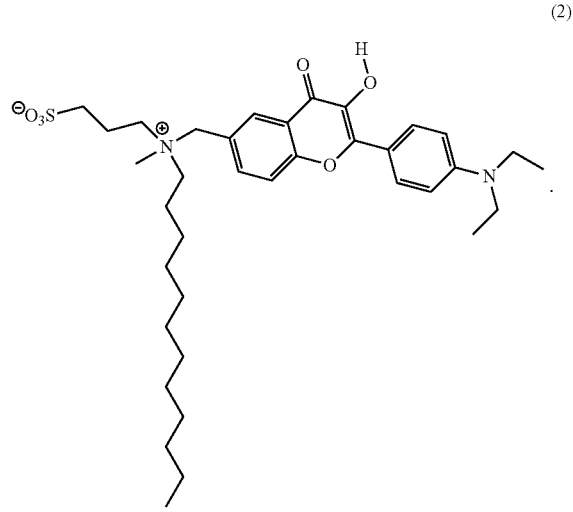

7. A process for preparing the compound according to claim 6, comprising the following steps:
   a. reacting 6-bromomethyl-4'-(diethylamino)-3-hydroxyflavone with dodecylmethylamine to form the corresponding tertiary amine (4'-(diethylamino)-6-(dodecyl (methyl)aminomethyl)-3-hydroxyflavone); and,
   b. reacting the product of step a. with propansultone to form the compound of formula (2).

8. The compound according to claim 5, having the specific formula (3):

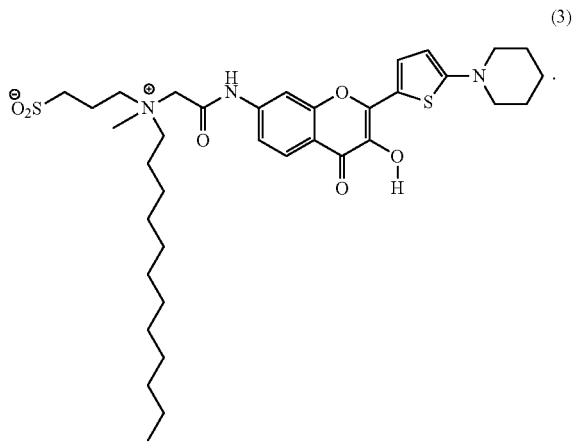

9. A process for preparing the compound according to claim 8, comprising the following steps:
   a. reacting N1-(4-acetyl-3-hydroxyphenyl)acetamide with 5-piperidino-2-thiophenecarbaldehyde in the presence of an alkoxide base followed by addition of excess of hydrogen peroxide and alkoxide base to form N1-[3-hydroxy-2-(5-piperidino-2-thienyl)-7-chromonyl]acetamide;
   b. hydrolysing N1-[3-hydroxy-2-(5-piperidino-2-thienyl)-7-chromonyl]acetamide in an acid affording 7-amino-3-hydroxy-2-(5-piperidino-2-thienyl)chromone;

c. reacting the product of b. with chloroacetylchloride which results in N1-[3-hydroxy-2-(5-piperidino-2-thienyl)-7-chromonyl]-2-chloroacetamide;

d. reacting the product of c. with dodecylmethylamine to form corresponding tertiary amine (N1-[3-hydroxy-2-(5-piperidino-2-thienyl)-7-chromonyl]-2-dodecyl(methyl)aminoacetamide, and e. reacting the product of d. with propansultone to form compound of formula (3).

10. The compound according to claim 5, having the specific formula (4):

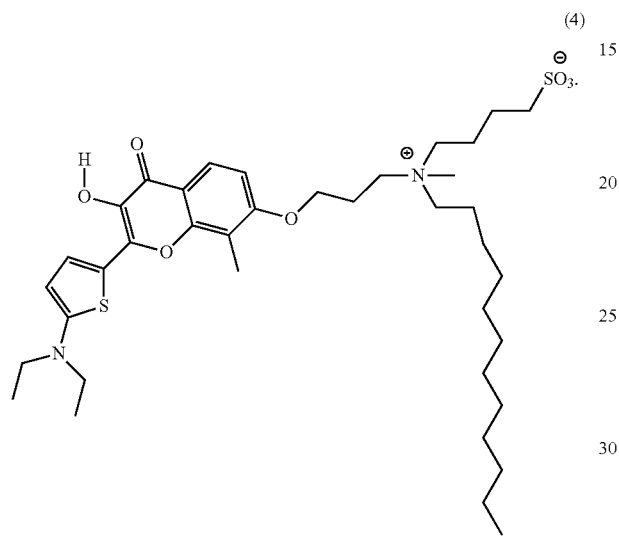

(4)

11. A process for preparing the compound according to claim 10, comprising the following steps:

a. reacting 3-methyl-2,4-dihydroxyacetophenone with a base followed by the addition of 1-bromo-3-chloro-propane to form 4-(3-chloropropoxy)-3-methyl-2-hydroxyacetophenone, b. reacting the product of step a. with N-methyldodecylamine in the presence of a base and iodide, to form 4-[3-(Dodecylmethylamino)-propoxy]-3-methyl-2-hydroxyacetophenone, c. reacting the product of step b. with 5-(1-(N,N-diethylamino))-2-thiophenecarbaldehyde in the presence of a base and a peroxide, preferably sodium methoxide and hydrogen peroxide, respectively, to form 2-(5-Diethylaminothiophen-2-yl)-7-[3-(dodecylmethylamino)-propoxy]-8-methyl-3-hydroxychromone, d. reacting the product of step c. with propansultone to form compound of formula (4).

12. The process of claim 11, wherein the base of steps a. and b. is potassium carbonate.

13. A method for detecting apoptosis in a population of cells, comprising the following steps: i) contacting the compound of claim 1 with the cells; ii) incubating said cells; iii) washing the cells; and, iv) detecting the apoptotic cells by observing the fluorescence emission spectra of the probe at an excitation wavelength from 350 to 500 nm.

14. A method to assess apoptosis in eukaryotic cells, comprising the following steps:
   i) contacting the compound of claim 1 with the cells;
   ii) incubating said cells;
   iii) washing the cells; and,
   iv) detecting the changes in the membrane composition of the cells by
      a. collecting the emission spectra of the compound inserted into an apoptotic cell by exciting said compound with an excitation wavelength from 350 to 500 nm,
      b. selecting the T* band and the N* band in the emission spectra; and,
      c. quantifying the loss of asymmetry of the cell plasma membrane during apoptosis by dividing the intensity of the T* band by the intensity of the N* band.

15. Method for Identifying compounds that induce or modulate apoptosis, comprising the following steps:
   i) contacting a test compound with a population of cells;
   ii) incubating said cells with said test compound;
   iii) washing the cells;
   iv) detecting apoptotic cells by contacting the compound of claim 1 with the cells, incubating said cells; washing the cells and measuring the fluorescence emission spectra of the probe at an excitation wavelength from 350 to 500 nm; and
   v) comparing the results with those obtained with a control compound.

16. A Method for following the evolution of a disease in a patient, said disease associated with lipid asymmetry of cell plasma membrane during apoptosis comprising the following steps: i) contacting the compound of claim 1 with a patient sample comprising cells; ii) incubating said cells; iii) washing the cells; and, iv) detecting the apoptotic cells by observing the fluorescence emission spectra of the probe at an excitation wavelength from 350 to 500 nm.

17. Method according to claim 16, wherein said disease are selected from the group consisting of Alzheimer's disease, Parkinson's disease, heart failure and cancers.

18. A Method for following the evolution of a disease in a patient, said disease associated with the apoptosis of cells comprising the following steps: i) contacting the compound of claim 1 with a patient sample comprising cells; ii) incubating said cells; iii) washing the cells; and, iv) detecting the changes in the membrane composition of the cells by a. collecting the emission spectra of the compound inserted into an apoptotic cell by exciting said compound with an excitation wavelength from 350 to 500 nm, b. selecting the T* band and the N* band in the emission spectra; and, c. quantifying the loss of asymmetry of the cell plasma membrane during apoptosis by dividing the intensity of the T* band by the intensity of the N* band.

19. A kit for detecting and/or quantifying and/or isolating apoptotic or necrotic cells comprising the compound of claim 1, optionally combined with a second reagent.

20. Kit according to claim 19, wherein the second reagent is propidium iodide.

* * * * *